US010219837B2

(12) United States Patent
Jackson et al.

(10) Patent No.: US 10,219,837 B2
(45) Date of Patent: Mar. 5, 2019

(54) BONE ANCHOR RECEIVER WITH LONGITUDINALLY EXTENDING TOOL ATTACHMENT STRUCTURES

(71) Applicant: Roger P. Jackson, Prairie Village, KS (US)

(72) Inventors: Roger P. Jackson, Prairie Village, KS (US); James L. Surber, Kansas City, KS (US)

(73) Assignee: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 15/836,383

(22) Filed: Dec. 8, 2017

(65) Prior Publication Data

US 2018/0098795 A1    Apr. 12, 2018

Related U.S. Application Data

(63) Continuation of application No. 13/385,997, filed on Mar. 20, 2012, and a continuation-in-part of application No. 13/373,289, filed on Nov. 9, 2011, now Pat. No. 9,907,574, said application No. 13/385,997 is a continuation-in-part of application No. 12/924,802, filed on Oct. 5, 2010, now Pat. No. 8,556,938, said application No. 13/385,997 is a continuation-in-part of application No. 12/072,354, filed on Feb. 26, 2008, now Pat. No. 10,076,361, and a continuation-in-part of application No. 11/126,965, filed on May 10, 2005, now Pat. No. 7,476,239, and a continuation-in-part of application No. 12/008,067, filed on Jan. 8, 2008, now Pat. No. 7,901,437.

(60) Provisional application No. 61/465,812, filed on Mar. 24, 2011, provisional application No. 61/456,649, filed on Nov. 10, 2010, provisional application No. 61/460,234, filed on Dec. 29, 2010, provisional application No. 61/287,240, filed on Oct. 5, 2009, provisional application No. 61/336,911, filed on Jan.
(Continued)

(51) Int. Cl.
*A61B 17/70*    (2006.01)
*A61B 17/86*    (2006.01)

(52) U.S. Cl.
CPC ...... *A61B 17/7032* (2013.01); *A61B 17/7037* (2013.01); *A61B 17/864* (2013.01)

(58) Field of Classification Search
CPC ..................................... A61B 17/70–17/7037
See application file for complete search history.

(56) References Cited

U.S. PATENT DOCUMENTS 6,063,090 A    5/2000    Schlapfer
7,530,992 B2    5/2009    Biedermann et al.
(Continued)

*Primary Examiner* — Eduardo C Robert
*Assistant Examiner* — Michelle C Eckman
(74) *Attorney, Agent, or Firm* — Polsinelli PC

(57) ABSTRACT

A polyaxial bone screw assembly includes a threaded shank body having an integral shank head receivable in a one-piece receiver having an upper channel for receiving a longitudinal connecting member and a lower cavity cooperating with a lower opening. A compression insert (some with an independent tool lock, lock and release feature and/or friction fit feature) and a split retaining ring articulatable with respect to both the shank head and the receiver (prior to locking) cooperate with the receiver to provide for pop- or snap-on assembly of the shank with the receiver either prior to or after implantation of the shank into a vertebra.

9 Claims, 12 Drawing Sheets

Related U.S. Application Data 28, 2010, provisional application No. 61/343,737, filed on May 3, 2010, provisional application No. 61/395,564, filed on May 14, 2010, provisional application No. 61/395,752, filed on May 17, 2010, provisional application No. 61/396,390, filed on May 26, 2010, provisional application No. 61/398,807, filed on Jul. 1, 2010, provisional application No. 61/400,504, filed on Jul. 29, 2010, provisional application No. 61/402,959, filed on Sep. 8, 2010, provisional application No. 61/403,696, filed on Sep. 20, 2010, provisional application No. 61/403,915, filed on Sep. 23, 2010, provisional application No. 60/905,472, filed on Mar. 7, 2007, provisional application No. 60/897,723, filed on Jan. 26, 2007.

(56) References Cited

U.S. PATENT DOCUMENTS

| | | | |
|---|---|---|---|
| 7,833,251 B1 | 11/2010 | Ahlgren et al. | |
| 8,876,869 B1 | 11/2014 | Schafer | |
| RE46,431 E * | 6/2017 | Jackson | A61B 17/7028 |
| 2002/0026193 A1 | 2/2002 | Barker et al. | |
| 2004/0267264 A1* | 12/2004 | Konieczynski | A61B 17/7032 |
| | | | 606/289 |
| 2005/0187548 A1 | 8/2005 | Butler | |
| 2005/0261687 A1* | 11/2005 | Garamszegi | A61B 17/7011 |
| | | | 606/305 |
| 2005/0277928 A1 | 12/2005 | Boschert et al. | |
| 2006/0200131 A1* | 9/2006 | Chao | A61B 17/7037 |
| | | | 606/278 |
| 2007/0055240 A1* | 3/2007 | Matthis | A61B 17/7037 |
| | | | 606/308 |
| 2007/0055244 A1* | 3/2007 | Jackson | A61B 17/7028 |
| | | | 606/86 A |
| 2007/0118123 A1 | 5/2007 | Strausbaugh | |
| 2007/0270831 A1 | 11/2007 | Dewey et al. | |
| 2008/0045953 A1 | 2/2008 | Garamszegi | |
| 2008/0140135 A1 | 6/2008 | Konieczynski et al. | |
| 2008/0154315 A1* | 6/2008 | Jackson | A61B 17/7037 |
| | | | 606/309 |
| 2008/0188898 A1* | 8/2008 | Jackson | A61B 17/7032 |
| | | | 606/305 |
| 2009/0062866 A1* | 3/2009 | Jackson | A61B 17/7032 |
| | | | 606/301 |
| 2009/0062867 A1 | 3/2009 | Schumacher | |
| 2009/0171391 A1* | 7/2009 | Hutton | A61B 17/7032 |
| | | | 606/246 |
| 2009/0254125 A1* | 10/2009 | Predick | A61B 17/7037 |
| | | | 606/264 |
| 2010/0036443 A1* | 2/2010 | Hutton | A61B 17/7032 |
| | | | 606/86 R |
| 2010/0094349 A1 | 4/2010 | Hammer et al. | |
| 2011/0040338 A1* | 2/2011 | Jackson | A61B 17/7032 |
| | | | 606/305 |
| 2012/0035670 A1* | 2/2012 | Jackson | A61B 17/7032 |
| | | | 606/305 |
| 2012/0046699 A1* | 2/2012 | Jones | A61B 17/7037 |
| | | | 606/305 |
| 2012/0046700 A1* | 2/2012 | Jackson | A61B 17/7037 |
| | | | 606/305 |
| 2012/0059426 A1* | 3/2012 | Jackson | A61B 17/7008 |
| | | | 606/300 |
| 2012/0078307 A1* | 3/2012 | Nihalani | A61B 17/7004 |
| | | | 606/264 |
| 2012/0143266 A1* | 6/2012 | Jackson | A61B 17/7008 |
| | | | 606/328 |
| 2012/0150239 A1* | 6/2012 | Garamszegi | A61B 17/7032 |
| | | | 606/328 |
| 2012/0179212 A1* | 7/2012 | Jackson | A61B 17/7032 |
| | | | 606/328 |
| 2012/0209336 A1* | 8/2012 | Jackson | A61B 17/7032 |
| | | | 606/305 |
| 2012/0245640 A1* | 9/2012 | Auerbach | A61B 17/7035 |
| | | | 606/264 |
| 2013/0060293 A1* | 3/2013 | Jackson | A61B 17/7037 |
| | | | 606/305 |
| 2013/0103098 A1* | 4/2013 | Jackson | A61B 17/8605 |
| | | | 606/305 |
| 2013/0144346 A1* | 6/2013 | Jackson | A61B 17/8605 |
| | | | 606/305 |
| 2013/0289631 A1* | 10/2013 | Jackson | A61B 17/7032 |
| | | | 606/304 |
| 2013/0345761 A1* | 12/2013 | Biedermann | A61B 17/7035 |
| | | | 606/306 |
| 2014/0107708 A1* | 4/2014 | Biedermann | A61B 17/7082 |
| | | | 606/278 |
| 2014/0236239 A1* | 8/2014 | Biedermann | A61B 17/7037 |
| | | | 606/278 |
| 2014/0276894 A1* | 9/2014 | Ramsay | A61B 17/7076 |
| | | | 606/104 |
| 2014/0277159 A1* | 9/2014 | Spratt | A61B 17/7037 |
| | | | 606/278 |
| 2014/0303675 A1* | 10/2014 | Mishra | A61B 17/7037 |
| | | | 606/279 |
| 2015/0080955 A1* | 3/2015 | Celmerowski | A61B 17/7005 |
| | | | 606/254 |
| 2015/0374413 A1* | 12/2015 | Spangler | A61B 17/7032 |
| | | | 606/266 |
| 2016/0317191 A1* | 11/2016 | Jones | A61B 17/7037 |
| 2017/0035462 A1* | 2/2017 | George | A61B 17/7038 |
| 2017/0095272 A1* | 4/2017 | Hutton | A61B 17/708 |
| 2017/0119449 A1* | 5/2017 | Jones | A61B 17/8866 |
| 2017/0135729 A1* | 5/2017 | Garamszegi | A61B 17/7032 |
| 2017/0209185 A1* | 7/2017 | Trautwein | A61B 17/7037 |
| 2017/0238976 A1* | 8/2017 | Higaki | A61B 17/7083 |
| 2017/0265903 A1* | 9/2017 | Longtain | A61B 17/7037 |
| 2017/0296234 A1* | 10/2017 | Jackson | A61B 17/7037 |
| 2017/0296235 A1* | 10/2017 | Chandanson | A61B 17/7032 |
| 2017/0319245 A1* | 11/2017 | Gephart | A61B 17/7043 |
| 2017/0333083 A1* | 11/2017 | Jackson | A61B 17/7035 |
| 2017/0354441 A1* | 12/2017 | Jackson | A61B 17/7052 |
| 2017/0360482 A1* | 12/2017 | Spratt | A61B 17/7037 |
| 2017/0360491 A1* | 12/2017 | Spratt | A61B 17/8685 |

\* cited by examiner

BONE ANCHOR RECEIVER WITH LONGITUDINALLY EXTENDING TOOL ATTACHMENT STRUCTURES

CROSS-REFERENCE TO RELATED APPLICATIONS

This application is a continuation of U.S. application Ser. No. 13/385,997 filed Mar. 20, 2012, which application claims the benefit of U.S. Prov. Pat. App. Ser. No. 61/465,812, filed Mar. 24, 2011 and incorporated by reference herein. Application Ser. No. 13/385,997 is also a continuation-in-part of U.S. patent application Ser. No. 13/373,289 filed Nov. 9, 2011 that claims the benefit of U.S. Prov. Pat. App. Ser. No. 61/456,649 filed Nov. 10, 2010 and U.S. Prov. Pat. App. Ser. No. 61/460,234 filed Dec. 29, 2010, all of which are incorporated by reference herein. Application Ser. No. 13/385,997 is also a continuation-in-part of U.S. patent application Ser. No. 12/924,802 filed Oct. 5, 2010, now U.S. Pat. No. 8,556,938, that claims the benefit of the following U.S. Prov. Pat. App. Ser. Nos. 61/278,240, filed Oct. 5, 2009; 61/336,911, filed Jan. 28, 2010; 61/343,737 filed May 3, 2010; 61/395,564 filed May 14, 2010; 61/395,752 filed May 17, 2010; 61/396,390 filed May 26, 2010; 61/398,807 filed Jul. 1, 2010; 61/400,504 filed Jul. 29, 2010; 61/402,959 filed Sep. 8, 2010; 61/403,696 filed Sep. 20, 2010; and 61/403,915 filed Sep. 23, 2010, all of which are incorporated by reference herein. Application Ser. No. 13/385,997 is also a continuation-in-part of U.S. patent application Ser. No. 12/072,354 filed Feb. 26, 2008 that claims the benefit of U.S. Prov. Pat. App. Ser. No. 60/905,472 filed Mar. 7, 2007 and is a continuation-in-part of U.S. patent application Ser. No. 11/126,965 filed May 10, 2005, now U.S. Pat. No. 7,476,239 and is a continuation-in-part of U.S. patent application Ser. No. 12/008,067 filed Jan. 8, 2008, now U.S. Pat. No. 7,901,437, that claims the benefit of U.S. Prov. App. Ser. No. 60/897,723 filed Jan. 26, 2007, all of which are incorporated by reference herein.

BACKGROUND OF THE INVENTION

The present invention is directed to polyaxial bone screws for use in bone surgery, particularly spinal surgery and particularly to such screws with compression or pressure inserts and expansion-only split retainers to snap over, capture and retain the bone screw shank head in the receiver member assembly and later fix the bone screw shank with respect to the receiver assembly.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw. Generally, the screws must be inserted into the bone as an integral unit along with the head, or as a preassembled unit in the form of a shank and pivotal receiver, such as a polyaxial bone screw assembly.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include similar open ends for receiving rods or portions of other fixation and stabilization structure.

A common approach for providing vertebral column support is to implant bone screws into certain bones which then in turn support a longitudinal structure such as a rod, or are supported by such a rod. Bone screws of this type may have a fixed head or receiver relative to a shank thereof, or may be of a polyaxial screw nature. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred. Also, it is often desirable to insert the bone screw shank separate from the receiver or head due to its bulk which can get in the way of what the surgeon needs to do. Such screws that allow for this capability are sometimes referred to as modular polyaxial screws.

With specific reference to modular snap-on or pop-on polyaxial pedicle screw systems having shank receiver assemblies, the prior art has shown and taught the concept of the receiver and certain retainer parts forming an assembly wherein a contractile locking engagement between the parts is created to fix the shank head with respect to the receiver and retainer. The receiver and shank head retainer assemblies in the prior art have included a slotted contractile retainer ring and/or a lower pressure slotted insert with an expansion and contraction collet-type of structure having contractile locking engagement for the shank head due to direct contact between the retainer and/or the collet structure with the receiver resulting in contraction of the slotted retainer ring and/or the collet-type structure of the insert against the shank head. The receiver and slotted insert have generally included tapered locking engagement surfaces.

The prior art for modular polyaxial screw assemblies has also shown and taught that the contact surfaces on the outside of the slotted collet and/or retainer and the inside of the receiver, in addition to being tapered, can be conical, radiused, spherical, curvate, multi-curvate, rounded, as well as other configurations to create a contractile type of locking engagement for the shank head with respect to the receiver.

In addition, the prior art for modular polyaxial screw assemblies has shown and taught that the shank head can both enter and escape from a collet-like structure on the insert or from the retainer when the insert or retainer is in the up position and within an expansion recess or chamber of the receiver. This is the case unless the slotted insert and/or the slotted retainer are blocked from being able to be pushed back up into receiver bore or cavity, or unless the screw assemblies are otherwise uniquely configured to prevent this from happening.

SUMMARY OF THE INVENTION

The present invention differentiates from the prior art by not allowing the receiver to be removed from the shank head once the parts are snapped-on and connected. This is true even if the retainer can go back up into the expansion chamber. This approach or design has been found to be more secure and to provide more resistance to pull-out forces compared to the prior art for modular polyaxial screw designs. Collect-like structures extending downwardly from lower pressure inserts, when used in modular polyaxial screw designs, as shown in the prior art, have been found to be somewhat weak with respect to pull-out forces encountered during some spinal reduction procedures. The present invention is designed to solve these problems.

The present invention also differentiates from the prior art by providing an expansion-only split or open retainer ring that is ultimately positioned in sliding, pivoting relation with the shank and positioned substantially below the shank head hemisphere in the receiver and can be a stronger, more substantial structure to resist larger pull-out forces on the assembly. Furthermore, the slitted or slotted retainer ring is also ultimately in sliding, pivoting relation with an inner surface of the receiver. The expansion only retainer has been found to be stronger and more secure when compared to that of the prior art which uses some type of contractile locking engagement between the parts, as described above; and, again, once assembled it cannot be disassembled.

Thus, a polyaxial bone screw assembly according to the invention includes a shank having an integral upper portion illustrated as a spherical head and a body for fixation to a bone; a separate receiver defining an upper open channel, a central bore, a lower cavity and a lower opening; a compression insert; and a resilient expansion-only split retainer for capturing the shank head in the receiver lower cavity, the retainer being slidingly engageable with both the shank head and a surface defining the receiver cavity. Thus, a first polyaxial articulation is formed by the shank head and the retainer and a second polyaxial articulation is formed by the retainer and the receiver making a compound articulation. In the illustrated embodiment, the shank upper portion or head is convex, more specifically, spherical, and the retainer has an inner concave surface, also illustrated as spherical, in slidable, pivoting and rotational relation thereto. The retainer also has an outer convex surface, illustrated as spherical, and the receiver has an inner concave surface, illustrated as spherical, in slidable, pivoting and rotational relation thereto. Thus, cooperation between the retainer and the shank head at one side thereof and the receiver at the other side thereof allows for multiple or, again, compound articulation of the shank with respect to the receiver.

It is foreseen in some embodiments when assembled with the receiver, retainer and insert, but prior to locking, that the shank head can be frictionally engaged with, but still movable in a non-floppy manner with respect to the insert to allow for movement of the shank to a desired position or angular orientation of the shank with respect to the receiver. For example, this could be done with a tool. The insert operatively engages the shank head and is spaced from the retainer by the shank head. The shank can be finally locked into a fixed position relative to the receiver by frictional engagement between a portion of the insert due to a downward force placed on the compression insert by a temporary locking tool or by a closure top pressing on a rod, or other longitudinal connecting member, captured within the receiver bore and channel. In the illustrated embodiments, retainers and inserts are downloaded into the receiver, but uploaded retainer embodiments are also foreseen. The shank head can be positioned into the receiver lower cavity at the lower opening thereof prior to or after insertion of the shank into bone. It is also foreseen that some compression inserts may include a lock and release feature for independent locking of the polyaxial mechanism so the screw can be used like a fixed monoaxial screw. In some embodiments the shank can be cannulated for minimally invasive surgery applications. The lower pressure insert and/or the retainer are both devoid of any type of receiver-retainer contractile locking engagements with respect to the shank head, and the receiver is devoid of any spring-tab like members.

Again, a pre-assembled receiver, compression insert and split retainer may be "pushed-on", "snapped-on" or "popped-on" to the shank head prior to or after implantation of the shank into a vertebra. Such a "snapping on" procedure includes the steps of uploading the shank head into the receiver lower opening, the shank head pressing against the base of the split retainer ring and expanding the resilient retainer out into an expansion portion or chamber of the receiver cavity followed by an elastic return of the retainer back to an original or near nominal shape thereof after the hemisphere of the shank head or upper portion passes through the ring-like retainer. In such neutral or original shape, the retainer is slidable with respect to both a lower portion of the shank head and an inner surface defining the receiver cavity, the illustrated retainer, shank and receiver surfaces being substantially spherical, with the retainer having an inner partially spherical surface and an outer partially spherical surface. However, it is foreseen that other surface configurations or combinations may be utilized. In the illustrated embodiment, the ultimate locking of the shank between the compression insert and the retainer is the result of a locking expansion-type of contact between the shank head and the split retainer and an expansion-type of non-tapered locking engagement between the retainer ring and a lower portion of the receiver cavity. The retainer can expand more in an upper portion of the receiver cavity to allow the shank head to pass through, but has restricted expansion to retain the shank head when the retainer is against the lower receiver surfaces defining the receiver cavity. The shank head is forced down against the retainer during final locking. It is foreseen that in some embodiments, when the polyaxial mechanism is locked, the insert could be forced or wedged against surfaces of the receiver resulting in an interference, non-contractile locking engagement, allowing for adjustment or removal of the rod or other connecting member without loss of a desired angular relationship between the shank and the receiver. This type of independent, non-contractile locking feature would allow the polyaxial screw to function like a fixed monoaxial screw, which could be very helpful in some applications.

The compression or pressure insert (a lock and release embodiment or a non-locking embodiment) may also be configured to be independently locked (permanently or temporarily) by a tool or instrument, thereby allowing the pop-on polyaxial screw to be distracted, compressed and/or rotated along and around the rod to provide for improved spinal correction techniques. Such a tool engages the pop-on receiver from the sides and then engages the insert to force or wedge the insert down into a locked position on the shank within the receiver. With the tool still in place and the correction maintained, the rod is then locked within the receiver channel by a closure top followed by removal of the tool. This process may involve multiple screws all being manipulated simultaneously with multiple tools to achieve the desired correction.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

Figure 1:
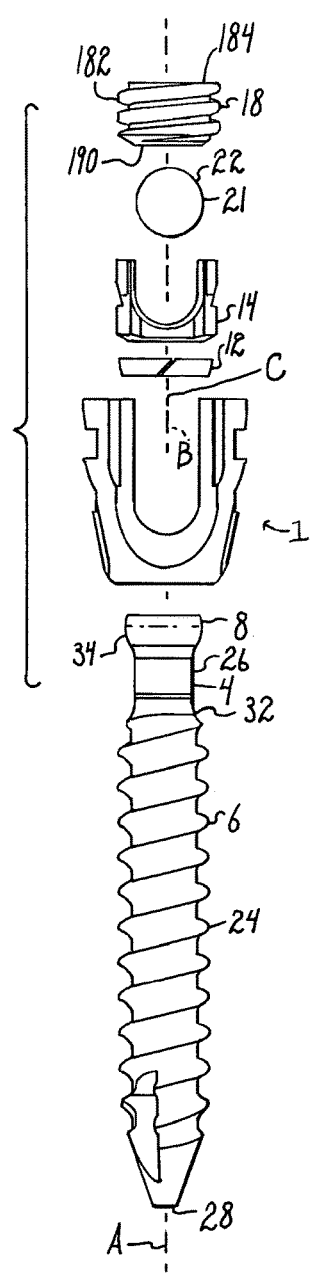
FIG. 1 is an exploded perspective view of a polyaxial bone screw assembly according to the present invention including a shank, a receiver, a retainer in the form of an open ring articulatable with respect to both the shank and the receiver and a crown compression insert, further shown with a portion of a longitudinal connecting member in the form of a rod and a closure top.
Figure 37:
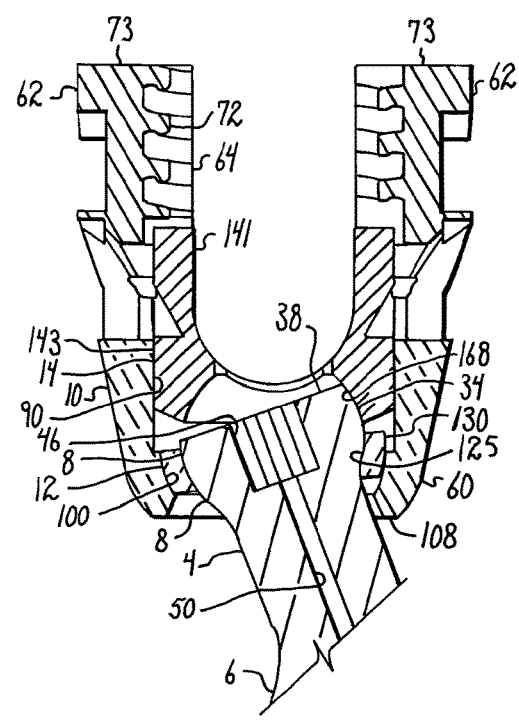
FIG. 37 is a partial front elevational view of the assembly of FIG. 35, further showing the shank and the retainer being articulated at an angle with respect to the receiver.
Figure 38:
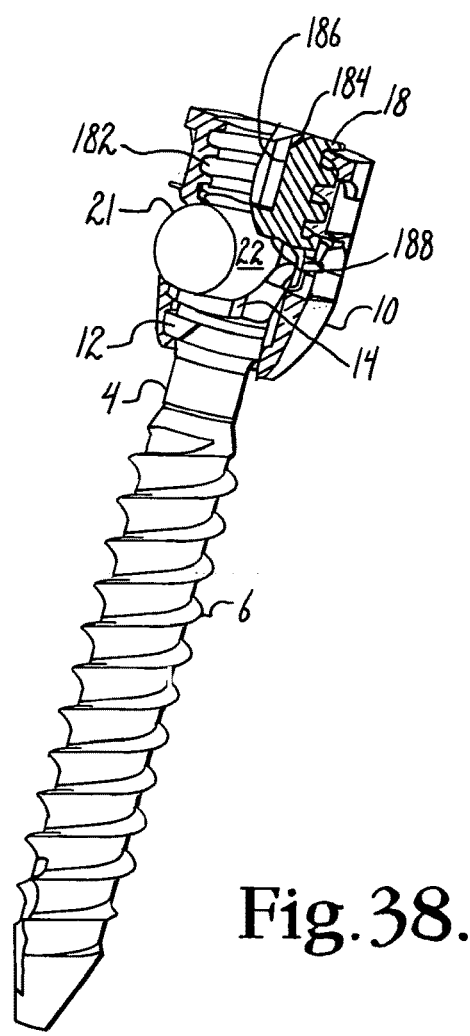
FIG. 38 is a reduced perspective view of the assembly of FIG. 35 further shown in engagement with the rod and closure of FIG. 1 and with portions broken away to show the detail thereof.

With reference to FIGS. 1-38 the reference number 1 generally represents a polyaxial bone screw apparatus or assembly according to the present invention. The assembly 1 includes a shank 4, that further includes a body 6 integral with an upwardly extending upper portion or head-like capture structure 8; a receiver 10; a retainer structure illustrated as a resilient open, articulatable ring 12, and a compression or pressure insert 14. The receiver 10, retainer 12 and compression insert 14 are initially assembled and may be further assembled with the shank 4 either prior or subsequent to implantation of the shank body 6 into a vertebra 17, as will be described in greater detail below. FIGS. 1 and 38 further show a closure structure 18 for capturing a longitudinal connecting member, for example, a rod 21 which in turn engages the compression insert 14 that presses against the shank upper portion 8 into fixed frictional contact with the retainer 12, so as to capture, and fix the longitudinal connecting member 21 within the receiver 10 and thus fix the member 21 relative to the vertebra 17. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure. The illustrated rod 21 is hard, stiff, non-elastic and cylindrical, having an outer cylindrical surface 22. It is foreseen that in other embodiments, the rod 21 may be elastic, deformable and/or of a different cross-sectional geometry. In such cases, the closure top could deform the rod and press directly on the insert 14.

Figure 2:
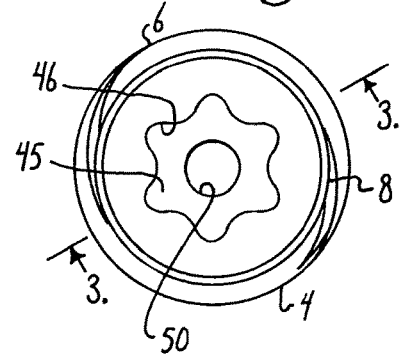
FIG. 2 is an enlarged top plan view of the shank of FIG. 1.
Figure 3:
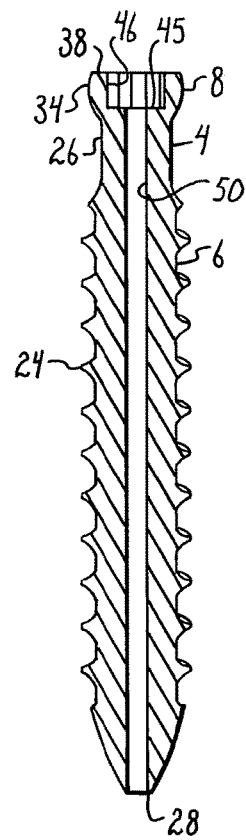
FIG. 3 is reduced cross-sectional view taken along the line 3-3 of FIG. 2.
Figure 4:
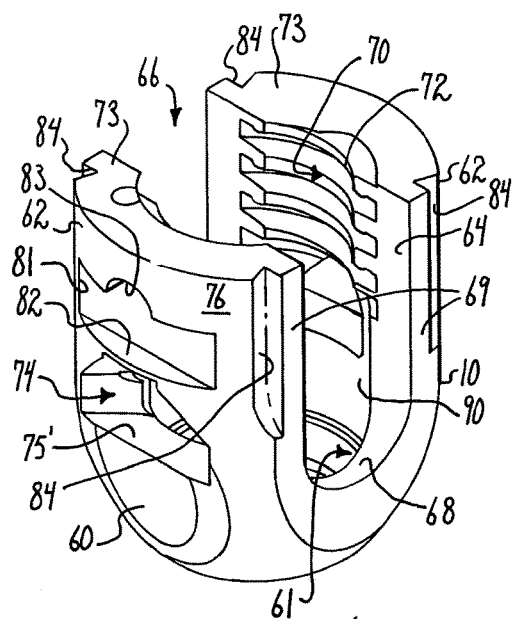
FIG. 4 is an enlarged perspective view of the receiver of FIG. 1.
Figure 5:
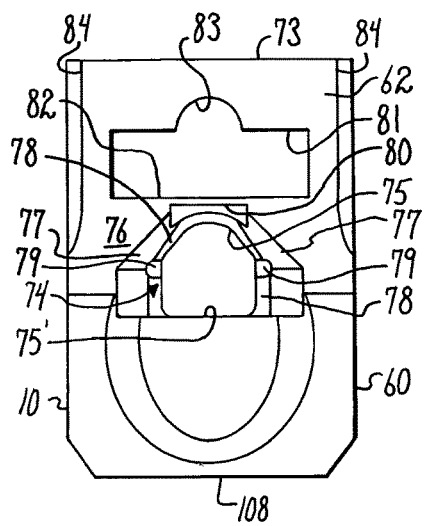
FIG. 5 is a side elevational view of the receiver of FIG. 4.
Figure 6:
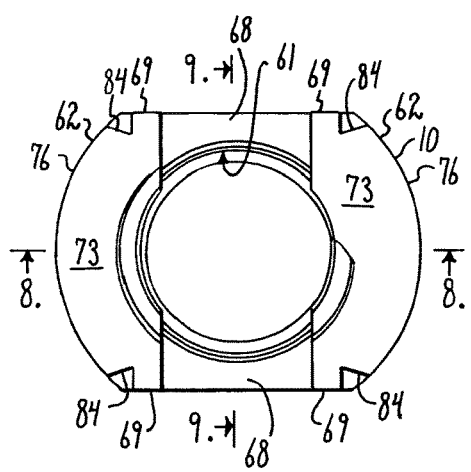
FIG. 6 is a top plan view of the receiver of FIG. 4.
Figure 7:
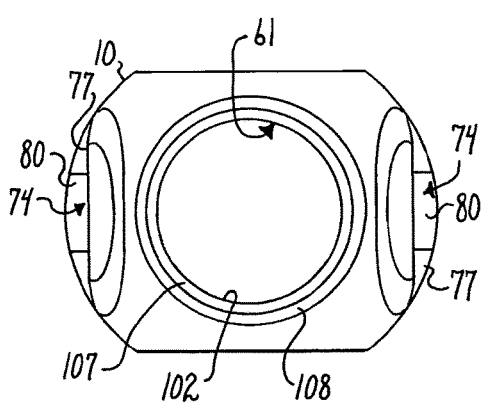
FIG. 7 is a bottom plan view of the receiver of FIG. 4.
Figure 8:
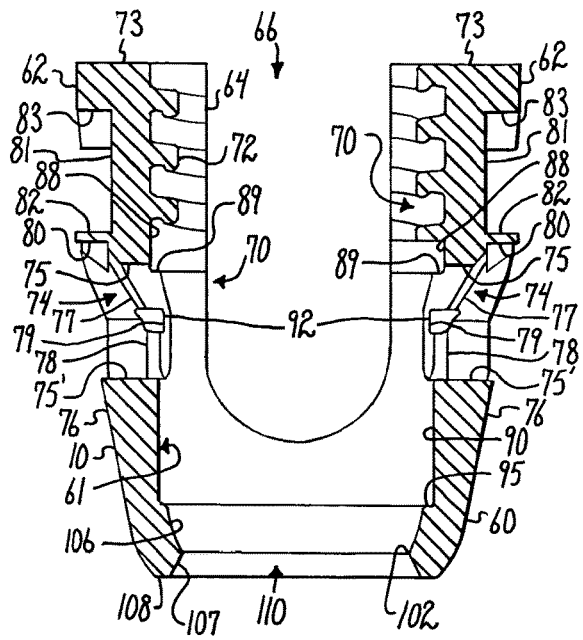
FIG. 8 is an enlarged cross-sectional view taken along the line 8-8 of FIG. 6.
Figure 9:
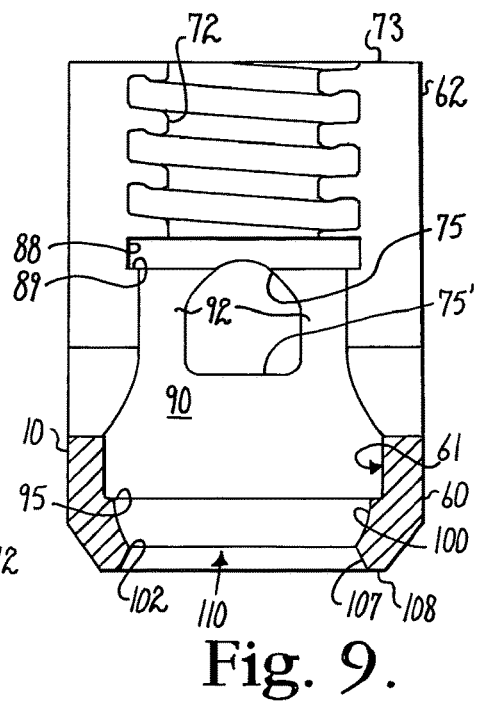
FIG. 9 is an enlarged cross-sectional view taken along the line 9-9 of FIG. 6.
Figure 10:
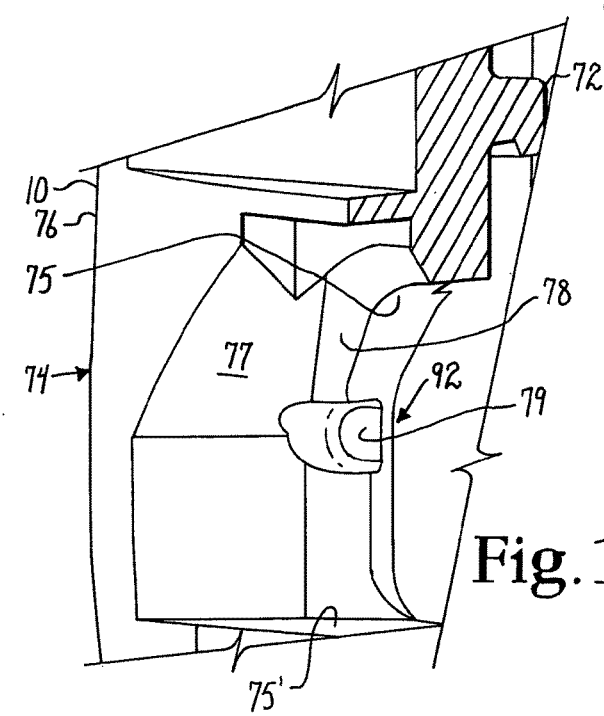
FIG. 10 is an enlarged and partial perspective view of a portion of the receiver of FIG. 4 with portions broken away to show the detail thereof.
Figure 11:
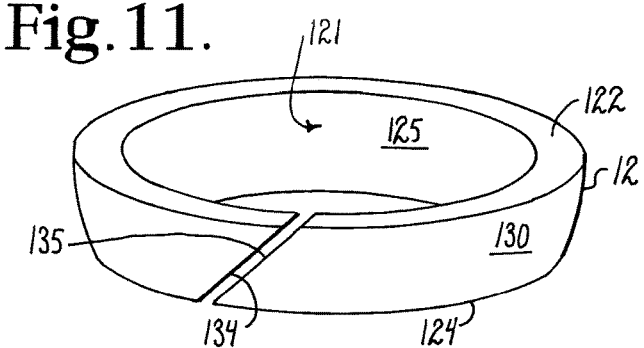
FIG. 11 is an enlarged perspective view of the retainer of FIG. 1.
Figure 12:
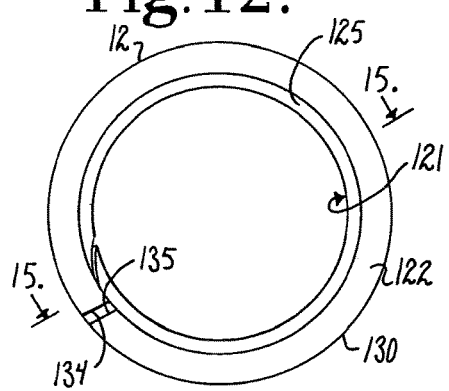
FIG. 12 is a reduced top plan view of the retainer of FIG. 11.
Figure 13:
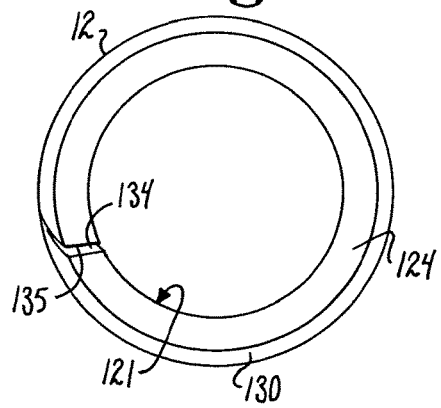
FIG. 13 is a bottom plan view of the retainer of FIG. 12.
Figure 14:
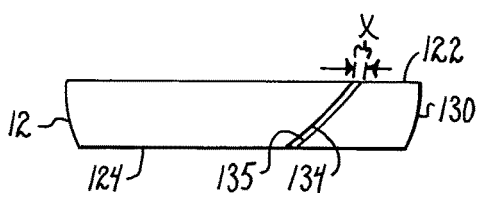
FIG. 14 is a front elevational view of the retainer of FIG. 12.
Figure 15:
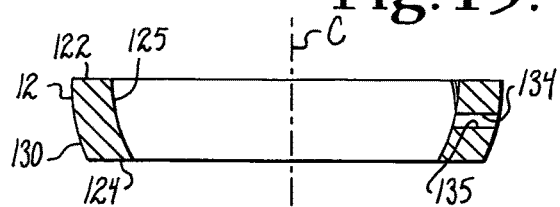
FIG. 15 is a cross-sectional view taken along the line 15-15 of FIG. 12.
Figure 16:
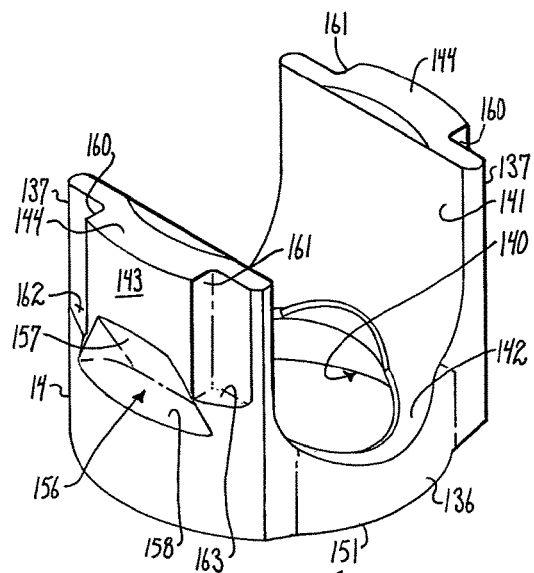
FIG. 16 is an enlarged perspective view of the insert of FIG. 1.
Figure 17:
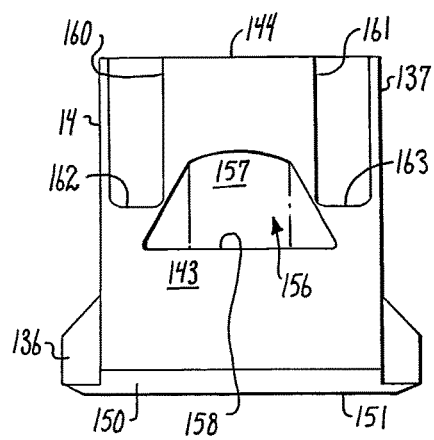
FIG. 17 is a side elevational view of the insert of FIG. 16.
Figure 18:
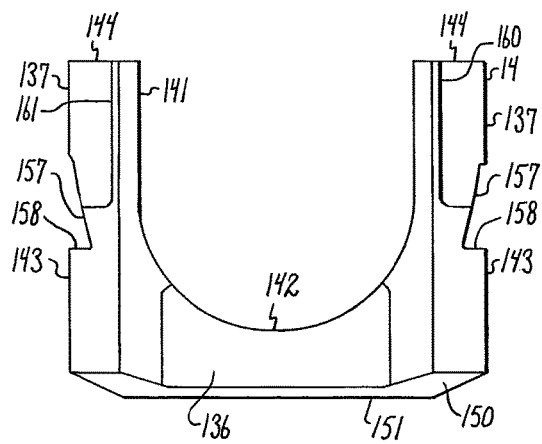
FIG. 18 is a front elevational view of the insert of FIG. 16.
Figure 19:
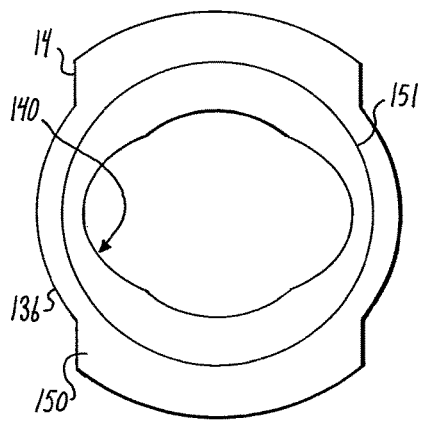
FIG. 19 is a bottom plan view of the insert of FIG. 16.
Figure 20:
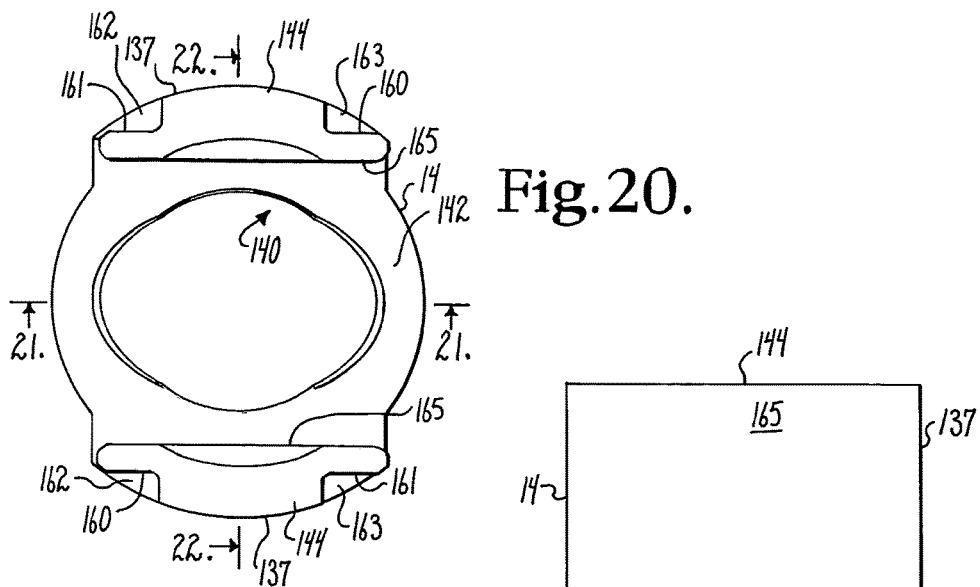
FIG. 20 is a top plan view of the insert of FIG. 16.
Figure 21:
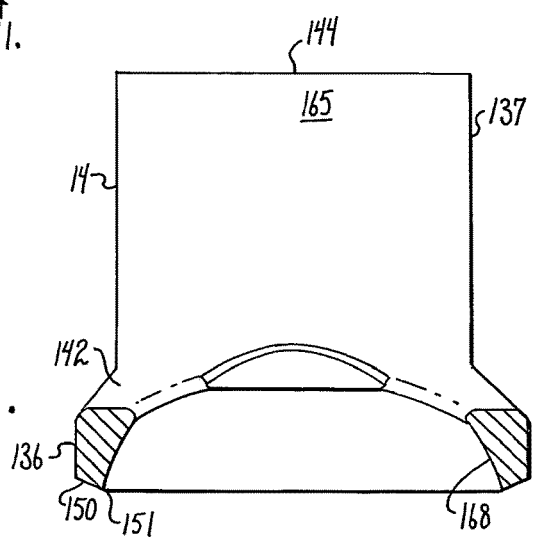
FIG. 21 is an enlarged cross-sectional view taken along the line 21-21 of FIG. 20.
Figure 22:
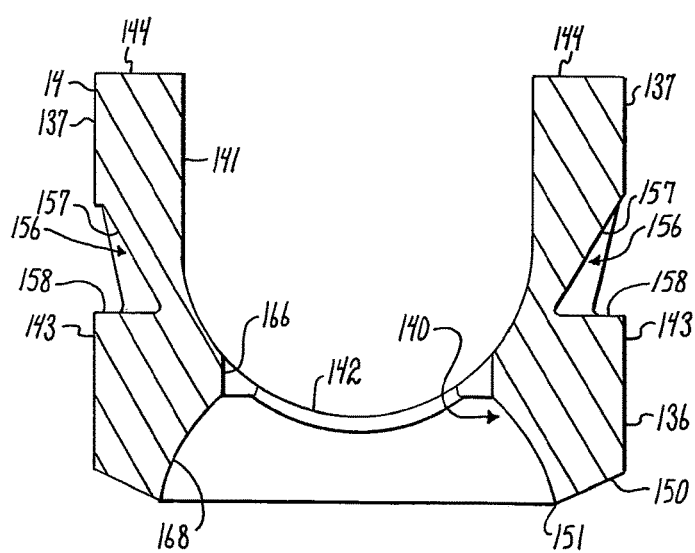
FIG. 22 is an enlarged cross-sectional view taken along the line 22-22 of FIG. 20.
Figure 23:
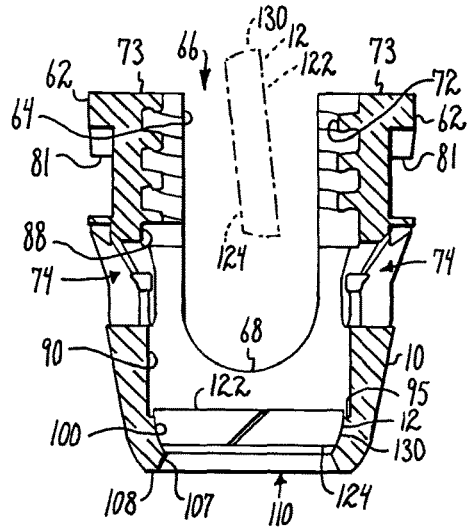
FIG. 23 is an enlarged front elevational view of the retainer and receiver of FIG. 1 with portions of the receiver broken away to show the detail thereof and further showing in phantom an intermediate position of the retainer while being downloaded into the receiver.

The shank 4, best illustrated in FIGS. 1-3, is elongate, with the shank body 6 having a helically wound bone implantable thread 24 (single or dual lead thread form) extending from near a neck 26 located adjacent to the upper portion or head 8, to a tip 28 of the body 6 and extending radially outwardly therefrom. During use, the body 6 utilizing the thread 24 for gripping and advancement is implanted into the vertebra 17 (e.g., see FIG. 29) leading with the tip 28 and driven down into the vertebra with an installation or driving tool (not shown), so as to be implanted in the vertebra to a location at or near the neck 26, as more fully described in the paragraphs below. The shank 4 has an elongate axis of rotation generally identified by the reference letter A.

The neck 26 extends axially upward from the shank body 6. The neck 26 may be of the same or is typically of a slightly reduced radius as compared to an adjacent upper end or top 32 of the body 6 where the thread 24 terminates. Further extending axially and outwardly from the neck 26 is the shank upper portion or head 8 that provides a connective or capture apparatus disposed at a distance from the upper end 32 and thus at a distance from the vertebra 17 when the body 6 is implanted in such vertebra.

The shank upper portion 8 is configured for a pivotable connection between the shank 4 and the retainer 12 and receiver 10 prior to fixing of the shank 4 in a desired position with respect to the receiver 10. The shank upper portion 8 has an outer, convex and substantially spherical surface 34 that extends outwardly and upwardly from the neck 26 and terminates at a substantially planar top or rim surface 38. The spherical surface 34 has an outer radius configured for frictional, sliding cooperation with a concave surface of the compression insert 14, as well as ultimate frictional engagement with the insert as will be discussed more fully in the paragraphs below. The top surface 38 is substantially perpendicular to the axis A. The spherical surface 34 shown in the present embodiment is substantially smooth, but in some embodiments may include a roughening or other surface treatment and is sized and shaped for cooperation and ultimate frictional engagement with the compression insert 14 as well as ultimate frictional engagement with the retainer 12. The shank spherical surface 34 is locked into place exclusively by the insert 14 and the retainer 12 and not by inner surfaces defining the receiver cavity, the shank being held in spaced relation with the receiver by the retainer 12.

A counter sunk substantially planar base 45 partially defines an internal drive feature or imprint 46. The illustrated internal drive feature 46 is an aperture formed in the top surface 38 and has a star shape designed to receive a driving tool (not shown) of an Allen wrench type, into the aperture for rotating and driving the bone screw shank 4. It is foreseen that such an internal tool engagement structure may take a variety of tool-engaging forms and may include one or more apertures of various shapes, such as a hex shape, a pair of spaced apart apertures or a multi-lobular or star-shaped aperture, such as those sold under the trademark TORX, or the like. The seat or base surface 45 of the drive feature 46 is disposed substantially perpendicular to the axis A with the drive feature 46 otherwise being coaxial with the axis A. The drive seat 45 may include beveled or stepped surfaces that may further enhance gripping with the driving tool. In operation, a driving tool (not shown) is received in the internal drive feature 46, being seated at the base 45 and engaging the plurality of faces of the drive feature 46 for both driving and rotating the shank body 6 into the vertebra 17, either before the shank 4 is attached to the receiver 10 or after the shank 4 is attached to the receiver 10, with the shank body 6 being driven into the vertebra 17 with the driving tool extending into the receiver 10.

The shank 4 shown in the drawings is cannulated, having a small central bore 50 extending an entire length of the shank 4 along the axis A. The bore 50 is defined by an inner cylindrical wall of the shank 4 and has a circular opening at the shank tip 28 and an upper opening communicating with the external drive 46 at the driving seat 45. The bore 50 is coaxial with the threaded body 6 and the upper portion 8. The bore 50 provides a passage through the shank 4 interior for a length of wire (not shown) inserted into the vertebra 17 prior to the insertion of the shank body 6, the wire providing a guide for insertion of the shank body 6 into the vertebra 17.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

Figure 29:
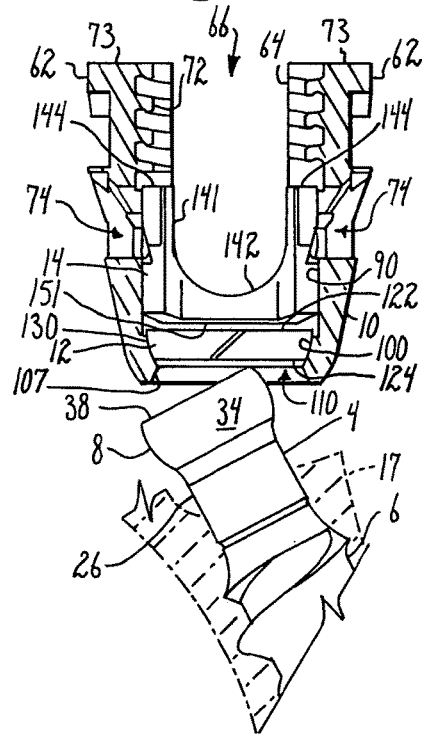
FIG. 29 is a reduced front elevational view with portions broken away, similar to FIG. 28 and further showing an alternative assembly stage with the shank of FIG. 1 shown in partial front elevation in which the shank is first implanted in a vertebra, shown in phantom, followed by assembly with the receiver, retainer and insert.

With particular reference to FIGS. 1 and 4-10, the receiver 10 has a generally U-shaped appearance with partially discontinuous and partially planar and cylindrical inner and outer profiles. The receiver 10 has an axis of rotation B that is shown in FIG. 1 as being aligned with and the same as the axis of rotation A of the shank 4, such orientation being desirable, but not required during assembly of the receiver 10 with the shank 4 (see, e.g., FIG. 29 showing the receiver 10 being "popped on" to a shank 4 that is implanted in a vertebra 17 and disposed at an angle with respect to the receiver). After the receiver 10 is pivotally attached to the shank 4, either before or after the shank 4 is implanted in a vertebra 17, the axis B is typically disposed at an angle with respect to the axis A, as shown, for example, in FIGS. 36 and 37.

The receiver 10 includes a partially curved or cylindrical and partially planar and diverging base 60 defining a bore or inner cavity, generally 61, the base 60 being integral with a pair of opposed upstanding arms 62 forming a cradle and defining a channel 64 between the arms 62 with an upper opening, generally 66, and a U-shaped lower channel portion or seat 68, the channel 64 having a width for operably snugly receiving the rod 21 or portion of another longitudinal connector between the arms 62; the channel 64 communicating with the base cavity 61. Outer front and rear opposed substantially planar arm surfaces 69 define an outer perimeter of the channel 64 at the arms 62 and about the channel seat 68.

Each of the arms 62 has an interior surface, generally 70, that includes various inner cylindrical profiles, an upper one of which is a partial helically wound guide and advancement structure 72 located adjacent top surfaces 73 of each of the arms 62. In the illustrated embodiment, the guide and advancement structure 72 is a partial helically wound interlocking flangeform configured to mate under rotation with a similar structure on the closure structure 18, as described more fully below. However, it is foreseen that for certain embodiments of the invention, the guide and advancement structure 72 could alternatively be a square-shaped thread, a buttress thread, a reverse angle thread or other thread-like or non-thread-like helically wound discontinuous advancement structures, for operably guiding under rotation and advancing the closure structure 18 downward between the arms 62, as well as eventual torquing when the closure structure 18 abuts against the rod 21 or other longitudinal connecting member. It is foreseen that the arms could have break-off extensions.

An opposed pair of rounded off triangular or delta-shaped tool receiving and engaging apertures, generally 74, each having a through bore formed by an upper arched surface 75 and a substantially planar bottom surface 75', are formed on outer surfaces 76 of the arms 62. Each through bore surface 75 and 75' extends through the arm inner surface 70. The apertures 74 with through bore portions 75 and 75' are sized and shaped for receiving locking, unlocking and other manipulation tools and may aid in receiving and downloading the retainer ring 12 during top loading of the retainer 12 into the receiver 10. Each aperture 74 further includes a sloping tool alignment surface 77 that generally surrounds the arched bore portion 75 and does not extend completely through the respective arm 62, the sloping surfaces 77 terminating at a substantially planar thin wall 78, the wall 78 defining the bore portion 75 and disposed at an angle to the wall 78. Each wall 78 further includes a further recessed crimping portion or area 79 that is also partially formed in one of the sloping surfaces 77. As will be described in greater detail below, during an assembly stage, each of the four crimping portions 79 is pressed or crimped into the insert 14 to aid in retaining the insert 14 in alignment with the receiver and prohibit rotation of the retainer with respect to the receiver, but to allow for movement of the retainer up and down along the receiver axis B. In a preferred embodiment, such up and down movement is possible only through the application of some upward or downward force, allowing for the insert to be placed in an out-of-the-way location during insertion of the shank head 8 through the retainer 12 and then later, for a non-floppy frictional engagement between the insert 14 and the shank upper portion 8 during intermediate assembly and/or implantation steps and positions prior to locking the shank into place between the insert 14 and the retainer 12. In other embodiments of the invention, other walls or surfaces defining the aperture 74 or other material defining other apertures or grooves may be inwardly crimped. It is noted that the illustrated receiver 10 is an integral structure and devoid of any spring tabs or collet-like structures. Alternatively, in some embodiments, spring tabs or other movable structure may be included on the receiver 10 or the insert 14 for retaining the insert 14 in a desired position, with regard to rotation and axial movement (along the axis A) with respect to the receiver 10. Preferably the insert and/or receiver are configured with structure for blocking rotation of the insert with respect to the receiver, but allowing some up and down movement of the insert with respect to the receiver during the assembly and implant procedure.

Formed in each surface 77 and also partially in each arm surface 76 and located opposite the planar surface 75' is another tool receiving recess 80 having a somewhat rectangular profile. A further recess 81 is located directly above the recess 80, the recess 81 being formed in each arm surface 76 and located between the aperture 74 and the arm top surface 73. Each recess 81 has a substantially rectangular profile with a base surface 82 that does not extend all the way through the respective arm 61 and further includes an upper curved portion 83 having a half-circular profile. Four V-shaped grooves 84 are formed in each of the arm surfaces 76 at each of the front and rear planar surfaces 69, each groove 84 running from the respective top surface 73 to a location midway along the receiver arm on either side of the aperture 74. Some or all of the apertures or grooves 74, 81 and 84 may be used for holding the receiver 10 during assembly with the insert 14, the retainer 12 and the shank 4; during the implantation of the shank body 6 into a vertebra when the shank is pre-assembled with the receiver 10; during assembly of the bone anchor assembly 1 with the rod 21 and the closure structure 18; and during lock and release adjustment of the some inserts of the invention with respect to the receiver 10, either into or out of frictional engagement with the inner surfaces of the receiver 10 as will be described in greater detail below. It is foreseen that tool receiving grooves, depressions or apertures may be configured in a variety of shapes and sizes and be disposed at other locations on the receiver arms 62.

Returning to the interior surface 70 of the receiver arms 62, located below the guide and advancement structure 72 is a discontinuous cylindrical surface 88 partially defining a run-out feature for the guide and advancement structure 72. The cylindrical surface 88 has a diameter equal to or slightly greater than a greater diameter of the guide and advancement structure 72. Moving downwardly in a direction toward the base 60, adjacent the cylindrical surface 88 of each, arm is a run-out seat or surface 89 that extends inwardly toward the axis B and slopes toward the axis B. Adjacent to and located below the surface 84 is another cylindrical surface 90 having a diameter smaller than the diameter of the surface 82. The through bore surfaces 75 and 75' extend through the arms primarily at the surfaces 90, with an upper portion of each arch 75 extending through one of the surfaces 88. Located near each aperture surface 75 is an inner surface portion 92 of the crimp areas or portions 79, the surface portions 92 engaging the insert 14 when the thin wall at the surface portion 79 is crimped toward the insert 14 during assembly of such insert in the receiver 10 as will be described in greater detail below. The inner discontinuous surface 90 found on the receiver arms 62 also extends downwardly into the receiver cavity 61 and thus defines an upper expansion area for the retainer 12. The surface 90 is disposed parallel to the receiver axis B and is sized to receive portions of the insert 14, and in some embodiments may be sized to provide a locking interference fit with a cylindrical portion of a locking insert.

Further, with respect to the base 60 and more specifically, the base cavity 61, a lower portion of the surface 90 that extends into the base and partially defines the base cavity 61 terminates at a stepped or sloping surface or surfaces 95 inwardly directed toward the axis B and sized and shaped to receive the retainer 12. The surface 90 defines a circumferential recess that is sized and shaped to receive the retainer 12 as it expands around the shank upper portion 8 as the shank 8 moves upwardly toward the channel 64 during assembly. The insert 14 provides an upper stop or restriction to prevent the expanded retainer 12 from moving upwardly with the shank portion 8, the insert 14 preventing the retainer 12 from passing upwardly out of the cavity 61 whether the retainer 12 is in a partially or fully expanded position or state. Adjacent and below the stepped or sloping surfaces 95 is an inner spherical surface 100 sized and shaped for sliding relation and ultimate frictional contact with an outer surface of the retainer 12 as will be described in greater detail below. The stepped surfaces 95 allow for sliding gradual movement of the retainer 12 into the space defined by the surface 100 and ultimate seating of the retainer 12 against the surface 100 and above and along a terminal edge 102 of the surface 100. Located below and adjacent to the edge 102 is a beveled or flared bottom opening surface 107, the surface 107 communicating with an exterior base surface 108 of the base 60, defining a lower opening, generally 110, into the base cavity 61 of the receiver 10.

With particular reference to FIGS. 1 and 11-15, the lower open or split retainer 12, that operates to capture the shank upper portion 8 within the receiver 10, has a central axis C that may be operationally the same or different than the axis B associated with the receiver 10 or the axis A associated with the shank 4 when the shank upper portion 8 and the retainer 12 are installed within the receiver 10. The retainer ring is thus articulatable and slidable with respect to both the shank 4 and the receiver 10 until locked into place. The retainer ring 12 is made from a resilient material, such as a stainless steel or titanium alloy, so that the retainer 12 may be expanded during various steps of assembly as will be described in greater detail below. The retainer 12 has a central channel or hollow through bore, generally 121, that passes entirely through the ring 12 from a top surface 122 to a bottom surface 124 thereof. The bore 121 is defined by an inner discontinuous spherical surface 125 that runs from adjacent the top surface 122 to adjacent the bottom surface 124. The retainer 12 further includes an outer spherical surface 130 that runs from adjacent the top surface 122 to adjacent the bottom surface 124. The inner spherical surface 125 is sized and shaped for closely slidingly receiving the shank head 8 at the surface 34 and ultimate frictional locking there-against and the outer spherical surface 130 is sized and shaped for close sliding engagement with the inner spherical surface 100 of the receiver 10 and ultimate frictional locking there-against. In some embodiments of the invention, spaced notches (not shown) may be formed in the spherical surface 130 to receive a holding and manipulation tool (not shown). In some embodiments further notches on inner or outer surfaces of the retainer may be made to evenly distribute stress across the entire retainer 12 during expansion thereof.

The resilient retainer 12 further includes first and second end surfaces, 134 and 135 disposed in spaced relation to one another when the retainer is in a neutral non-compressed state. The surface 134 and 135 may also be touching when the retainer is in a neutral state. Both end surfaces 134 and 135 run from the top surface 122 to the bottom surface 124 and are illustrated as running at an oblique angle to such top and bottom surfaces. In other embodiments of the invention, the surfaces 134 and 135 may be disposed substantially perpendicular to the top surface 122 and the bottom surface 124. A width X between the surfaces 134 and 135 is very narrow (slit may be made by EDM process) to provide stability to the retainer 12 during operation. Because the retainer 12 is top loadable in a neutral state and the retainer 12 does not need to be compressed to fit within the receiver cavity 61, the width X may be much smaller than might be required for a bottom loaded compressible retainer ring. The gap X functions only in expansion to allow the retainer 12 to expand about the shank upper portion 8. This results in a stronger retainer that provides more surface contact with the shank upper portion 8 upon locking, resulting in a sturdier connection with less likelihood of failure than a retainer ring having a greater gap. Furthermore, because the retainer 12 is only expanded and never compressed inwardly, the retainer 12 does not undergo the mechanical stress that typically is placed on spring ring type retainers known in the prior art that are both compressed inwardly and expanded outwardly during assembly. It is foreseen that in some embodiments of the invention, the retainer 12 inner surfaces may include a roughening or additional material to increase the friction fit against the shank upper portion 8 prior to lock down by the rod 21 or other longitudinal connecting member.

With particular reference to FIGS. 1 and 16-22, the crown compression insert 14 is illustrated that is sized and shaped to be received by and down-loaded into the receiver 10 at the upper opening 66. The compression insert 14 has an operational central axis that is the same as the central axis B of the receiver 10. In operation, the insert advantageously frictionally engages the bone screw shank upper portion 8, allowing for un-locked but non-floppy placement of the angle of the shank 4 with respect to the receiver 10 during surgery prior to locking of the shank with respect to the receiver near the end of the procedure. In some embodiments of the invention, the insert that has locked the shank 4 in a desired angular position with respect to the receiver 10, by, for example, compression from the rod 21 and closure top 18, may also be forced into an interference fit engagement with the receiver 10 at the inner cylindrical surface 90, for example, and thus be capable of retaining the shank 6 in a locked position even if the rod 21 and closure top 18 are removed. Such locked position may also be released by the surgeon if desired by features included in the insert 14, such as ridges, grooves and/or apertures, bores or holes. The non-locking insert 14 (as well as an alternative locking insert) is preferably made from a solid resilient material, such as a stainless steel or titanium alloy, so that portions of the insert may be snapped or popped onto the shank upper portion 8 as well as pinched or pressed against and un-wedged (in certain embodiments) from the receiver 10 with a release tool.

The non-locking crown collet compression insert 14 includes a substantially cylindrical body 136 integral with a pair of upstanding arms 137. A bore, generally 140, is disposed primarily within and through the body 136 and communicates with a generally U-shaped through channel formed by a saddle 141 that is partially defined by the upstanding arms 137 and partially by the body 136. The saddle 141 is sized and shaped to closely, snugly engage the cylindrical rod 21 and includes a curved lower seat 142. It is foreseen that an alternative embodiment may be configured to include planar holding surfaces that closely hold a square or rectangular bar as well as hold a cylindrical rod-shaped, cord, or sleeved cord longitudinal connecting member. The arms 137 disposed on either side of the saddle 141 extend upwardly from the body 136. The arms 137 are sized and configured for ultimate placement at or near the cylindrical run-out surface 88 and inner surface 90 located below the receiver guide and advancement structure 72. It is foreseen that in some embodiments of the invention, the insert arms 137 may be extended and the closure top configured such the arms ultimately directly engage the closure top 18 for locking of the polyaxial mechanism, for example, when the rod 21 is made from a deformable material. In such embodiments, the insert 14 would include a rotation blocking structure or feature on an outer surface thereof that abuts against cooperating structure located on an inner wall of the receiver 10, preventing rotation of the insert with respect to the receiver when the closure top is rotated into engagement with the insert, especially when there is no rod in place. In the present embodiment, each of the arms 137 includes an outer surface 143 that is illustrated as partially cylindrical and runs from the substantially planar top surfaces 144 to an inwardly sloping lower surface 150 of the insert 14, the surface 150 extending about the body 136 and the arms 137 and terminating at an annular rim or edge 151. The surface 150 is advantageously sloped or angled to provide clearance between the insert 14 and the retainer 12 when the retainer and shank 4 are articulated or pivoted with respect to one another and with respect to the receiver 10. Also, the sloping surface 150 that runs from the lower edge or rim 151 outwardly and upwardly away from the axis B and toward the upper surfaces 144 provides a sliding outwardly and upwardly directed surface for guiding the top surface 122 of the retainer 12 during expansion of the retainer inner spherical surface 125 about the shank head 8 spherical surface 34 as will be discussed in greater detail below.

The surfaces 143 are sized and shaped to generally fit within the receiver arms 62. The arm outer surfaces 143 further include notches or grooves formed thereon for receiving manipulation, unlocking and locking tools. Although not shown, each surface 143 may include one or more through bores or other apertures for receiving tooling, particularly useful for alternative locking embodiments (not shown). Centrally located (in some embodiments below a through bore) and formed in each surface 143 is a delta or triangular notch or recess, generally 156, for receiving tooling defined in part by an upper sloping surface 157 and intersecting a lower planar surface 158 disposed substantially perpendicular to a central axis of the insert 14 (and the axis B of the receiver when the insert is disposed within the receiver). Each of the surfaces 167 and surface 168 cooperate and align with the respective receiver aperture through bore surfaces 77 and 75' when the insert 14 is captured and operationally positioned within the receiver 10 as will be described in greater detail below. In the illustrated embodiments, also formed in each surface 143 are a pair of spaced v- or squared-off notches or grooves 160 and 161 that run from the respective top surface 144 to near the sloping surface 157 of the central delta cut or notch 156. The grooves 160 and 161 cooperate with the receiver crimp wall 79 inner surfaces 92 to aid in alignment of the insert channel saddle 141 with the receiver channel 64 as shown, for example in FIGS. 25-27. The illustrated pair of grooves 160 and 161 are disposed substantially parallel to the central axis of the insert 14, running from one of the top surfaces 144 to respective lower or bottom surfaces 162 and 163.

The u-shaped channel formed by the saddle 141 is also partially defined by opposed inner planar surfaces 165 located near the arm top surfaces 144. The saddle 141 also communicates with the bore 140 at an inner cylindrical surface 166, the surface 166 located centrally within the insert body 136 and further communicating with a lower concave surface portion 168 having a generally spherical profile with a radius the same or substantially similar to a radius of the surface 34 of the shank upper portion or head 8. The surface 168 terminates at the edge or rim 151. It is foreseen that in some embodiments of the invention a portion or all of the surface 168 may include ridges, stepped surfaces or a surface roughening or texture, such as scoring or knurling, or the like, for enhancing frictional engagement with the shank upper portion 8.

The insert bore 140 is sized and shaped to receive the driving tool (not shown) therethrough that engages the shank drive feature 46 when the shank body 6 is driven into bone with the receiver 10 attached. Also, in alternative locking embodiments, the bore 140 may receive a manipulation tool used for releasing the such insert from a locked position with the receiver, the tool pressing down on the shank and also gripping the insert at the opposed through bores or with other tool engaging features. A manipulation tool for un-wedging a locking insert from the receiver 10 may also access the such tooling bores from the receiver through bores 74. The illustrated insert 14 may further include other features, including grooves and recesses for manipulating and holding the insert 14 within the receiver 10 and providing adequate clearance between the retainer 12 and the insert 14.

The insert body 136 located between the arms 137 has an outer diameter slightly smaller than a diameter between crests of the guide and advancement structure 72 of the receiver 10, allowing for top loading of the compression insert 14 into the receiver opening 66, with the arms 137 of the insert 14 being located between the receiver arms 62 during insertion of the insert 14 into the receiver 10. Once the arms 137 of the insert 14 are generally located beneath the guide and advancement structure 72, the insert 14 is rotated into place about the receiver axis B until the top surfaces 144 are located directly below the guide and advancement structure 72 as will be described in greater detail below.

With reference to FIGS. 1 and 38, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface 22 of uniform diameter. The rod 21 may be made from a variety of metals, including hard and soft metal alloys and hard and soft or deformable and less compressible plastics, including, but not limited to rods made of elastomeric, polyetheretherketone (PEEK) and other types of materials.

Longitudinal connecting members for use with the assembly 1 may take a variety of shapes, including but not limited to rods or bars of oval, rectangular or other curved or polygonal cross-section. The shape of the insert 14 may be modified so as to closely hold, and if desired, fix or slidingly capture the longitudinal connecting member to the assembly 1. Some embodiments of the assembly 1 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from soft deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 38, the closure structure or closure top 18 shown with the assembly 1 is rotatably received between the spaced arms 62 of the receiver 10. It is noted that the closure 18 top could be a twist-in or slide-in closure structure. The illustrated closure structure 18 is substantially cylindrical and includes a an outer helically wound guide and advancement structure 182 in the form of a flange that operably joins with the guide and advancement structure 72 disposed on the arms 62 of the receiver 10. The flange form utilized in accordance with the present invention may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 18 downward between the arms 62 and having such a nature as to resist splaying of the arms 62 when the closure structure 18 is advanced into the channel 64, the flange form illustrated herein as described more fully in Applicant's U.S. Pat. No. 6,726,689 is preferred as the added strength provided by such flange form beneficially cooperates with and counters any reduction in strength caused by the inset surfaces 69 resulting in a reduced profile of the illustrated receiver 10 at the U-shape channel, such surfaces advantageously engaging longitudinal connecting member components as will be further described below. The illustrated closure structure 18 also includes a top surface 184 with an internal drive 186 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 166 is used for both rotatable engagement and, if needed, disengagement of the closure 18 from the receiver arms 62. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A base or bottom surface 188 of the closure is planar and further includes a rim 190 and may or may not include a further include a central point (not shown), the rim 190 and or the point (not shown) for engagement and penetration into the surface 22 of the rod 21 in certain embodiments of the invention. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 62.

Preferably the receiver 10, the retainer 12 and the compression insert 14 are assembled at a factory setting that includes tooling for holding, pressing and alignment of the component pieces as well as compressing or expanding the insert 14 arms, if needed, as well as crimping a portion of the receiver 10 toward the insert 14. In some circumstances, the shank 4 is also assembled with the receiver 10, the retainer 12 and the compression insert 14 at the factory. In other instances, it is desirable to first implant the shank 4, followed by addition of the pre-assembled receiver, retainer and compression insert at the insertion point. In this way, the surgeon may advantageously and more easily implant and manipulate the shanks 4, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 8 and/or hydroxyapatite on the shank 6), with the receiver, retainer and compression insert. Allowing the surgeon to choose the appropriately sized or treated shank 4 advantageously reduces inventory requirements, thus reducing overall cost.

Figure 24:
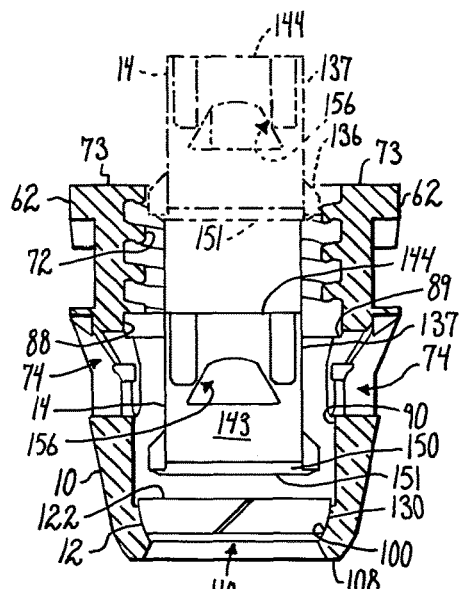
FIG. 24 is a front elevational view with portions broken away, similar to FIG. 23, further showing the insert of FIG. 1 in enlarged side elevation, with an early stage of assembly of the insert being shown in phantom.
Figure 25:
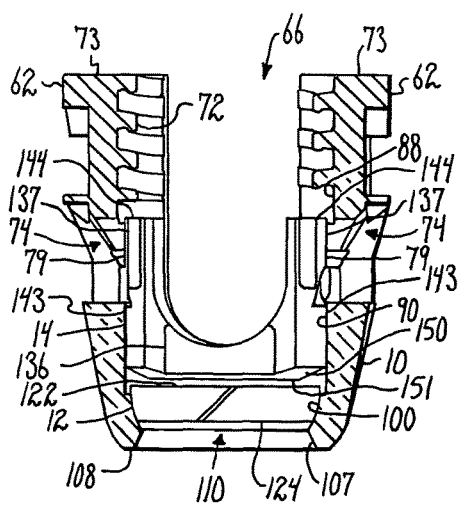
FIG. 25 is a front elevational view with portions broken away, similar to FIG. 24, showing the insert rotated within the receiver during an assembly stage subsequent to that shown in FIG. 24.
Figure 26:
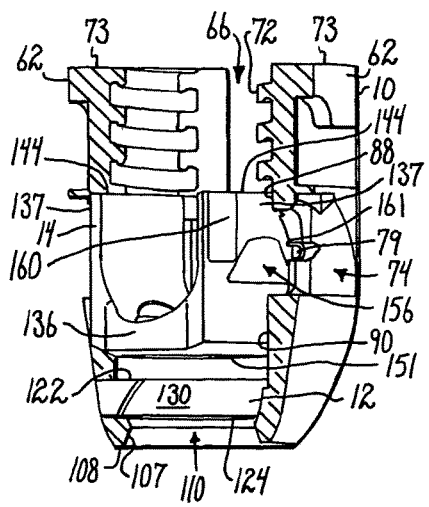
FIG. 26 is an enlarged perspective view with portions broken away of the assembly shown in FIG. 25 and further showing a subsequent step of crimping a portion of the receiver against the insert.
Figure 27:
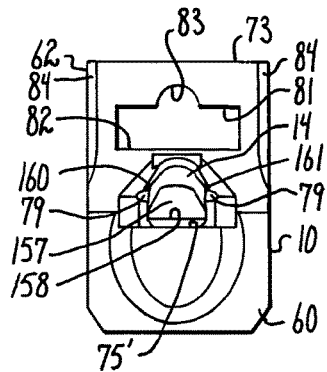
FIG. 27 is a reduced side elevational view of the assembly shown in FIG. 26.
Figure 28:
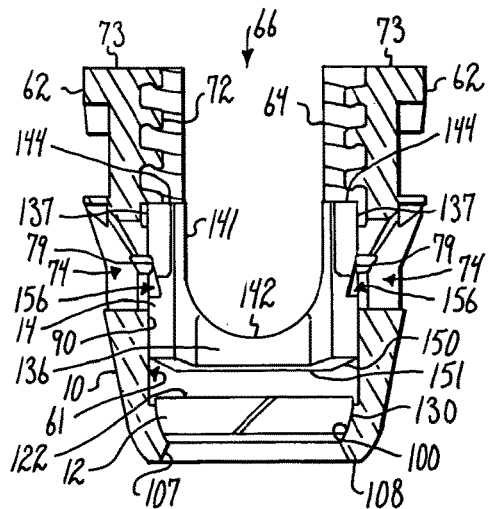
FIG. 28 is a front elevational view with portions broken away, similar to FIG. 25 and shown with the crimping of FIGS. 26 and 27.

Pre-assembly of the receiver 10, retainer 12 and compression insert 14 is shown in FIGS. 23-28. First, the retainer 12 is downloaded in a sideways manner into the receiver 10 through the upper opening 66 with the outer surface 130 facing the receiver channel seat 68. The retainer 12 is then lowered between the arms 62 and toward the receiver base 60 as shown in phantom in FIG. 23, the retainer being turned or tilted to a position within the receiver base 60 inner cavity 61 wherein the retainer bottom surface 124 is manipulated to a position facing the spherical surface 100 and then the surface 130 is seated upon the inner spherical surface 100 as shown in solid lines in FIG. 23. With reference to FIG. 24, the compression insert 14 is then downloaded into the receiver 10 through the upper opening 66 with the bottom rim 151 facing the receiver arm top surfaces 73 and the insert arms 137 located between the opposed receiver arms 62. The insert 14 is then lowered toward the channel seat 68 until the insert 14 arm upper surfaces 144 are adjacent the run-out area defined by the surfaces 88 of the receiver 10 located below the guide and advancement structure 72. Thereafter, the insert 14 is rotated in a clockwise or counter-clockwise manner about the receiver axis B until the upper arm surfaces 144 are directly below the guide and advancement structure 72 as illustrated in FIG. 25 with the U-shaped channel 141 of the insert 14 aligned with the U-shaped channel 64 of the receiver 10. In some embodiments, the insert arms 137 may need to be compressed slightly during rotation to clear inner surfaces of the receiver arms 62. As shown in FIGS. 25-27, the outer cylindrical surfaces 143 of the insert 14 are received within the cylindrical surfaces 88 and 90 of the receiver. With particular reference to FIGS. 26 and 27, the receiver thin walls of the crimping area 79 are then pressed inwardly toward the axis B by inserting a tool (not shown) into the receiver apertures 74, the tool pressing the sloped surface walls 77 until the receiver inner wall surfaces 92 engage the insert 14 at each of the grooves 160 and 161 formed into the outer cylindrical surface 143 of each of the insert arms 137. The crimping of the opposed wall surfaces 87 into the groves 160 and 161 keeps the insert 14 U-shaped channel 141 substantially aligned with the receiver U-shaped channel 64, but allows for upward and downward movement of the insert 14 along the receiver axis B during bottom loading of the shank 4 as shown in FIG. 29, for example. However, such upward and downward movement requires some force, as the four-point frictional engagement between the insert and the receiver advantageously keeps the insert at a desired axial location and is not a floppy or loose sliding engagement. Thus, the crimping of the receiver walls 77 prohibits rotation of the insert 14 about the receiver axis B but allows for limited axial movement of the insert 14 with respect to the receiver 10 along the axis B when some force is exerted to slide the crimped surfaces 87 up or down along the grooves 160 and 161. As illustrated in FIG. 28, the insert 14 arms 137 are fully captured within the receiver 10 by the guide and advancement structure 72 prohibiting movement of the insert 14 up and out through the receiver opening 66 as well as by the retainer 12 and the receiver annular surface 104 located in the receiver 10 base 60 below the insert 14. Also as illustrated in FIG. 28, the insert 14 may be desirably moved upwardly in the receiver 10 until an insert top surface 144 abuts against the guide and advancement structure 72. FIG. 28 illustrates a preferred arrangement for shipping of the receiver, retainer and insert combination as well as a preferred upward and out-of-the-way position for the insert 14 during assembly with the shank 4. In some embodiments of the invention, top or side surfaces of the insert 14 may include a resilient projection or projections for temporarily frictionally engaging with an inner surface of the receiver 10 to hold the insert 14 in an upper portion of the receiver 10 during some of the assembly steps, also providing a frictional but slidable fit between the insert 14 and the receiver 10.

At this time, the receiver, insert and retainer combination are ready for shipping to an end user, with both the compression insert 14 and the retainer 12 captured within the receiver 10 in a manner that substantially prevents movement or loss of such parts out of the receiver 10. The receiver 10, compression insert 14 and the retainer 12 combination may now be assembled with the shank 4 either at the factory, by surgery staff prior to implantation, or directly upon an implanted shank 4 as shown, for example, in FIG. 29, with the shank axis A and the receiver axis B either being aligned during assembly as shown in FIG. 30 and most of the drawings figures illustrating the assembly process, or the axes being at an angle with respect to one another as shown in FIG. 29.

As illustrated in FIG. 29, the bone screw shank 4 or an entire assembly 1 made up of the assembled shank 4, receiver 10, retainer 12 and compression insert 14, is screwed into a bone, such as the vertebra 17, by rotation of the shank 4 using a suitable driving tool (not shown) that operably drives and rotates the shank body 6 by engagement thereof at the internal drive 46. Specifically, the vertebra 17 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw shank 4 or the entire assembly 1 is threaded onto the guide wire utilizing the cannulation bore 50 by first threading the wire into the opening at the bottom 28 and then out of the top opening at the drive feature 46. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires. When the shank 4 is driven into the vertebra 17 without the remainder of the assembly 1, the shank 4 may either be driven to a desired final location or may be driven to a location slightly above or proud to provide for ease in assembly with the pre-assembled receiver, compression insert and retainer.

Figure 30:
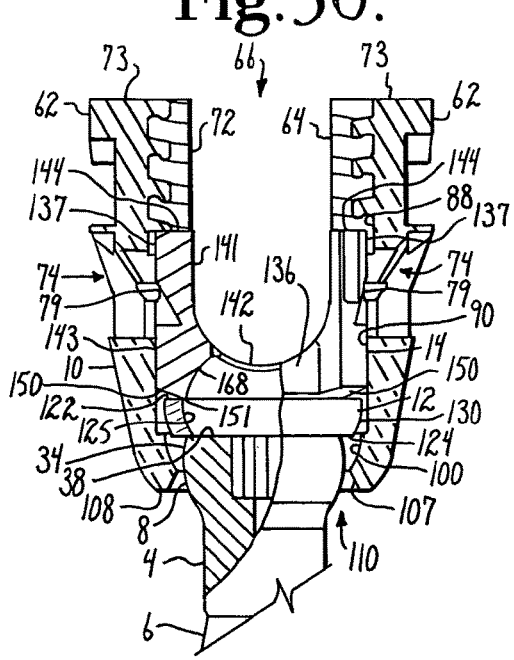
FIG. 30 is an enlarged and partial front elevational view with portions broken away, similar to FIG. 28 showing the shank (not implanted in a vertebra) in a stage of assembly with the retainer, the retainer being pushed up into engagement with the insert.
Figures 31, 32, 33:
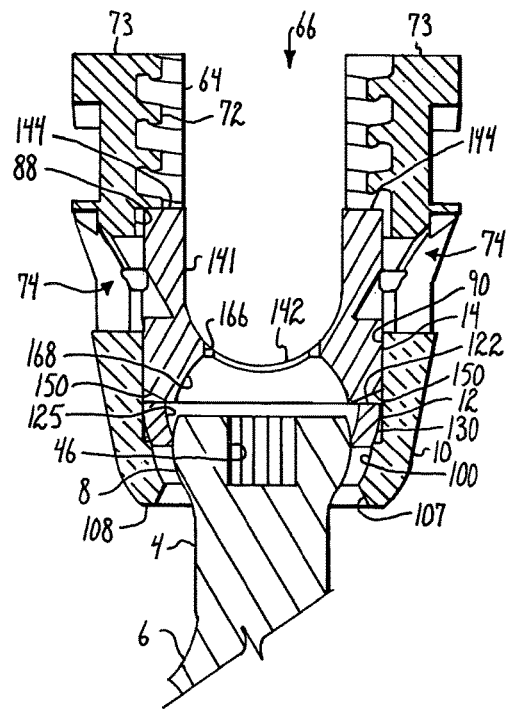
FIG. 31 is an enlarged partial front elevational view with portions broken away, similar to FIG. 30, and having further portions broken away showing the retainer in an expanded state about an upper portion of the shank.
FIG. 32 is a partial front elevational view with portions broken away, similar to FIG. 31, and showing a subsequent step of the retainer being returned to a neutral state capturing the shank within the receiver.
FIG. 33 is a partial front elevational view with portions broken away, similar to FIG. 32, the shank upper portion and retainer being pulled downwardly into the receiver.
Figure 34:
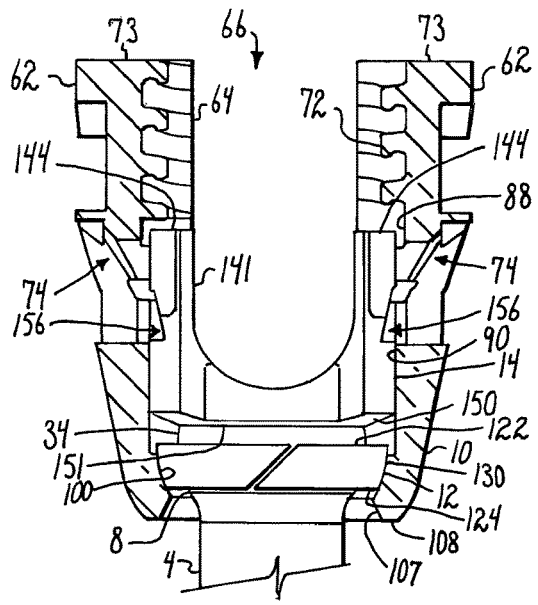
FIG. 34 is a partial front elevational view with portions broken away, similar to FIG. 33 showing a subsequent step of lowering the insert into engagement with the shank.

With reference to FIGS. 29, 30 and 31, the pre-assembled receiver, insert and retainer are placed above the shank upper portion 8 until the shank upper portion is received within the opening 110. As the shank upper portion 8 is moved into the interior 61 of the receiver base defined by the spherical surface 100, the shank upper portion 8 presses the retainer 12 upwardly into the portion of the receiver cavity 61 defined by the cylindrical surface 90. With particular reference to FIGS. 30 and 31, as the portion 8 continues to move upwardly toward the channel 64, the top surface 122 of the retainer 12 abuts against the lower or bottom frusto-conical or otherwise outwardly sloping surface 150 of the insert 14, limiting and directing upward movement of the retainer 12 and forcing outward movement of the retainer 12 towards the cylindrical surface 90 that defines an expansion area or chamber for the retainer 12 as the shank 4 continues to move upwardly with respect to the retainer 12. As is shown in FIGS. 30-32, the insert 14 is prohibited from moving upwardly in the receiver by contact between the insert arm top surface 144 with the receiver guide and advancement structure 72. With further reference to FIG. 31 and also with reference to FIGS. 32 and 33, the retainer 12 begins to contract about the spherical surface 34 as the center of the sphere of the head 8 passes beyond the center of the retainer expansion recess defined by the surface 125. At this time also, the spherical surface 34 moves into engagement with the insert 14 spherical surface 168.

Figure 36:
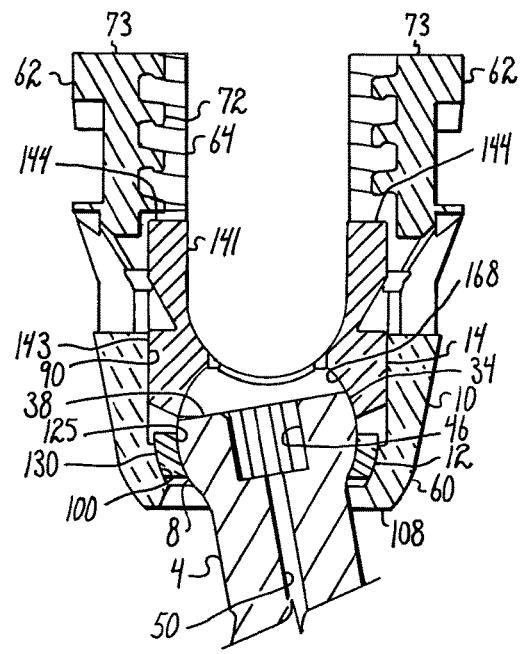
FIG. 36 is a partial front elevational view of the assembly of FIG. 35, further showing the shank being articulated at an angle with respect to the receiver.

With reference to FIG. 33, the shank 4 and retainer 12 may then be manipulated further downwardly into a desired seated position on the receiver inner spherical surface 100 by either an upward pull on the receiver 10 or, in some cases, by driving the shank 4 further into the vertebra 17. Then, with reference to FIG. 34, the insert 14 may be pressed downwardly with a tool (not shown) onto the shank head 8 spherical surface 34. At this time, the insert 14 surface 168 and the surface 34 are in a fairly tight friction fit, the surface 34 being pivotable with respect to the insert 14 with some force. Thus, a tight, non-floppy ball and socket joint is now created between the insert 14 and the shank upper portion 8 as well as between the retainer inner and outer surfaces and adjacent surfaces of the shank head 8 and the receiver seating surface 100. At this time, the receiver 10 and may be articulated to a desired angular position with respect to the shank 4, such as that shown in FIGS. 36 and 37, but prior to insertion of the rod or closure top, that will be held, but not locked, by the frictional engagement between the retainer 12, the shank upper portion 8 and the receiver 10. With reference to FIG. 36, angular pivoting or articulation of the shank 4 with respect to the retainer 12 is shown. With reference to FIG. 37, angular pivoting or articulation of the retainer 12 with respect to the receiver 10 is shown as well as articulation of the shank 4 with respect to the retainer 12.

With reference to FIG. 38, the rod 21 is eventually positioned in an open or percutaneous manner in cooperation with the at least two bone screw assemblies 1. The closure structure 18 is then inserted into and advanced between the arms 62 of each of the receivers 10. The closure structure 18 is rotated, using a tool engaged with the inner drive 186 until a selected pressure is reached at which point the rod 21 engages the U-shaped seating surface 142 of the compression insert 14, pressing the insert surface 168 into locked frictional engagement with the shank spherical surface 34. Specifically, as the closure structure 18 rotates and moves downwardly into the respective receiver 10, the rim 190 engages and penetrates the rod surface 22, the closure structure 18 pressing downwardly against and biasing the rod 21 into compressive engagement with the insert 14 that urges the shank upper portion 8 toward the retainer 12 and into locking engagement therewith, the retainer 12 frictionally abutting and expanding outwardly against the spherical surface 100. For example, about 80 to about 120 inch pounds of torque on the closure top may be applied for fixing the bone screw shank 4 with respect to the receiver 10.

An alternative lock-and-release compression insert (not shown) may be identical or substantially similar to the insert 14 previously described herein, with the exception that the locking insert is sized for a frictional interference fit with the receiver 10; specifically, a locking interference between the cylindrical inner surface 90 of the receiver 10 and a part or portion of the outer body surface 143 that is sized and shaped to have a greater diameter than the diameter of the illustrated surface 143. Such a locking insert would preferably further include a pair of opposed through bores extending through the insert arm surfaces or some other feature for receiving tooling for unlocking of such insert from the receiver. Such an insert may be assembled with the receiver 10, retainer 12, shank 4, rod 21 and closure top 18, in a manner the same as previously described above with respect to the assembly 1, with the exception that the alternative insert would be forced downwardly into a locking interference fit with the receiver 10 when the shank 4 is locked in place, as compared to the easily sliding relationship between the insert 14 and the receiver 10. One way in which to force the alternative insert into locking interference is by assembly with the rod and closure top. After being fully locked down, the closure top may be loosened or removed and/or the rod may be adjusted and/or removed and the frictional engagement between the alternative insert and the receiver 10 at the interferingly fixed surfaces would remain in place, advantageously maintaining a locked angular position of the shank 4 with respect to the receiver 10. At this time, another rod, such as a deformable rod and cooperating alternative closure top may be loaded onto the already locked-up assembly to result in an alternative assembly. The drive of such a closure top may advantageously be made smaller than the drive of the closure 18, such that the deformable rod is not unduly pressed or deformed during assembly since the polyaxial mechanism is already locked.

Figure 35:
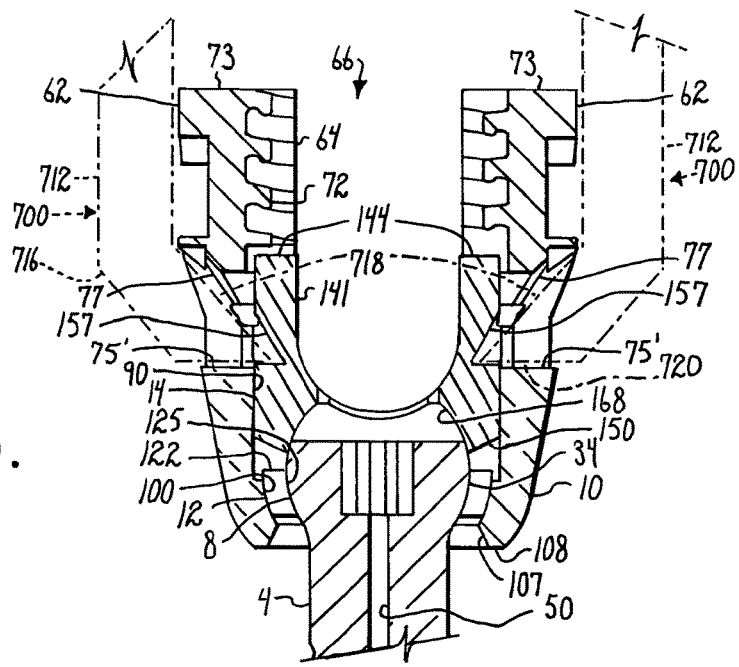
FIG. 35 is a partial front elevational view of the assembly as shown in FIG. 34 with further portions broken away to show the detail thereof.

With reference to FIG. 35, a temporary locking and manipulation tool, generally 700, is illustrated in phantom for independently, temporarily locking the insert 14 against the shank head 8 and thus temporarily locking the angle of the shank 4 with respect to the receiver 10. The tool 700 includes a pair of opposed arms 712, each having an engagement extension 716 positioned at an angle with respect to the respective arm 712 such that when the tool is moved downwardly toward the receiver, one or more inner surfaces 718 of the engagement extension 716 slide along the surfaces 77 of the receiver and along the surfaces 157 of the insert 14 to engage the insert 14, with a surface 720 pressing downwardly on the insert surfaces 158, pushing the insert downwardly and pressing the spherical surface 168 into locking frictional fit with the spherical surface 34 of the shank 4. It is foreseen that the tool 700 may include a variety of holding and pushing/pulling mechanisms, such as a pistol grip tool, that may include a ratchet feature, a hinged tool, or, a rotatably threaded device, for example for temporarily holding or fixing the polyaxial mechanism of the assembly 1 in a desired position or orientation.

It is to be understood that while certain forms of the present invention have been illustrated and described herein, it is not to be limited to the specific forms or arrangement of parts described and shown.

The invention claimed is:

1. A bone anchor receiver for securing an elongate rode to a bone anchor, the bone anchor receiver comprising:
   a base, and
   opposed spaced-a-part upright arms extending upward from the base to define an upward opening channel defined between the upright arms and having a first side opening and a second side opening, each upright arm including:
      an outer arm surface facing outward and on an opposite side of the upright arm from the channel,
      a top surface facing upward and extending between the respective outer arm surface and the channel; and
      first and second upward extending V-shaped grooves extending upwardly to intersect the respective top surface, the first upward extending V-shaped groove being adjacent the first side opening and the second upward extending V-shaped groove being adjacent the second side opening,
   wherein each upward extending V-shaped groove is further defined by two planar surfaces forming an acute angle therebetween.

2. The bone anchor receiver of claim 1, wherein the V-shaped grooves are formed in the outer arm surface of each upright arm and spaced from the channel.

3. The bone anchor receiver of claim 1, further comprising substantially planar outwardly-facing surfaces formed into the receiver arms adjacent the first side opening and the second side opening.

4. The bone anchor receiver of claim 3, wherein the V-shaped grooves are spaced from the channel by the substantially planar outwardly-facing surfaces.

5. The bone anchor receiver of claim 3, wherein the substantially planar outwardly-facing surfaces extend below the channel and into the base of the receiver.

6. A bone anchor receiver for securing an elongate rode to a bone anchor, the bone anchor receiver comprising:
   a base, and
   opposed spaced-a-part upright arms extending upward from the base to define an upward opening channel defined between the upright arms and having a front side opening and a rear side opening, each upright arm including:
      an outer arm surface facing outward and on an opposite side of the upright arm from the channel;
      a top surface facing upward and extending between the respective outer arm surface and the channel;
      front and rear outwardly-facing planar surfaces formed into each receiver arm adjacent the front side opening and the rear side opening, respectively, and defining an outer perimeter of the channel; and
      upward extending V-shaped grooves formed into each receiver arm at the front and rear planar surfaces and extending upwardly to intersect the respective top surface.

7. The bone anchor receiver of claim 6, wherein the upward extending V-shaped grooves are spaced from the channel by the front and rear planar surfaces.

8. The bone anchor receiver of claim 6, wherein each upward extending V-shaped groove is further defined by two planar surfaces forming an acute angle therebetween.

9. The bone anchor receiver of claim 6, wherein the front and rear planar surfaces extend below the channel and into the base of the receiver.

\* \* \* \* \*

UNITED STATES PATENT AND TRADEMARK OFFICE
CERTIFICATE OF CORRECTION

| | |
|---|---|
| PATENT NO. | : 10,219,837 B2 |
| APPLICATION NO. | : 15/836383 |
| DATED | : March 5, 2019 |
| INVENTOR(S) | : Jackson et al. |

It is certified that error appears in the above-identified patent and that said Letters Patent is hereby corrected as shown below:

On the Title Page

- In the Related U.S. Application Data item (63), in the first column second line, delete "and" and insert --which is--, therefore.

- In the Related U.S. Application Data item (63), in the first column ninth line, delete "and" and insert --which is--, therefore.

- In the Related U.S. Application Data item (60), in the second column third line, delete "61/287,240" and insert --61/278,240--, therefore.

Signed and Sealed this
Fifth Day of July, 2022

Katherine Kelly Vidal
*Director of the United States Patent and Trademark Office*